(12) United States Patent
Bidne et al.

(10) Patent No.: US 8,512,392 B2
(45) Date of Patent: Aug. 20, 2013

(54) STENT DESIGN WITH STRUTS OF VARIOUS ANGLES AND STIFFNESS

(75) Inventors: Ben Bidne, Buffalo, MN (US); Brian Tischler, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1093 days.

(21) Appl. No.: 11/716,209

(22) Filed: Mar. 9, 2007

(65) Prior Publication Data
US 2008/0221661 A1 Sep. 11, 2008

(51) Int. Cl.
*A61F 2/06* (2013.01)
(52) U.S. Cl.
USPC .......................................... 623/1.15
(58) Field of Classification Search
USPC ............ 623/1.12, 1.15, 1.18, 1.2, 1.16, 1.17, 623/1.19
See application file for complete search history.

(56) References Cited

U.S. PATENT DOCUMENTS

| | | | |
|---|---|---|---|
| 5,843,120 A | 12/1998 | Israel et al. | 606/198 |
| 5,861,027 A | 1/1999 | Trapp | 623/1 |
| 5,922,020 A * | 7/1999 | Klein et al. | 623/1.15 |
| 5,935,162 A | 8/1999 | Dang | |
| 6,013,854 A | 1/2000 | Moriuchi | 623/11 |
| 6,022,371 A | 2/2000 | Killion | 606/198 |
| 6,027,526 A | 2/2000 | Limon et al. | |
| 6,042,606 A | 3/2000 | Frantzen | |
| 6,299,635 B1 | 10/2001 | Frantzen | 623/1.17 |
| 6,309,414 B1 | 10/2001 | Rolando et al. | |
| 6,331,188 B1 | 12/2001 | Lau et al. | 623/1.13 |
| 6,355,057 B1 | 3/2002 | DeMarais et al. | |
| 6,423,090 B1 | 7/2002 | Hancock | |
| 6,540,774 B1 | 4/2003 | Cox | |
| 6,613,081 B2 | 9/2003 | Kim et al. | |
| 6,743,252 B1 | 6/2004 | Bates et al. | 623/1.15 |
| 6,846,323 B2 * | 1/2005 | Yip et al. | 623/1.16 |
| 6,896,696 B2 | 5/2005 | Doran et al. | |
| 6,939,373 B2 | 9/2005 | Gomez et al. | |
| 6,997,945 B2 | 2/2006 | St. Germain | 623/1.15 |
| 7,223,283 B2 | 5/2007 | Chouinard | 623/1.15 |
| 7,335,228 B2 | 2/2008 | Schaeffer | |
| 2002/0055770 A1 | 5/2002 | Doran et al. | 623/1.15 |
| 2002/0111669 A1 | 8/2002 | Pazienza et al. | 623/1.15 |

(Continued)

FOREIGN PATENT DOCUMENTS

| | | |
|---|---|---|
| WO | 96/26689 | 2/1996 |
| WO | 01/15632 A1 | 3/2001 |
| WO | 01/21095 A2 | 3/2001 |
| WO | 2006/035669 A1 | 4/2006 |

*Primary Examiner* — Ryan Severson
*Assistant Examiner* — Jonathan W Miles
(74) *Attorney, Agent, or Firm* — Vidas, Arrett & Steinkraus, P.A.

(57) ABSTRACT

The present invention is directed to stent that has a plurality of axially spaced serpentine bands. Each serpentine band comprises a plurality of struts, wherein adjacent struts are connected to each other forming a plurality of peaks and valleys. The plurality of struts comprise a plurality of adjacent pairs of struts, wherein each adjacent pair of struts comprises a first strut and a second strut and wherein the first and second struts have a first end, a second end and a length and a plurality of interconnecting struts axially connect the serpentine bands. The stent further includes a plurality of connector nodes, wherein a plurality of first and second struts that are associated with a connector node have a greater stiffness than a plurality of struts that are not associated with a connector node.

30 Claims, 17 Drawing Sheets

(56) References Cited

U.S. PATENT DOCUMENTS

| | | | |
|---|---|---|---|
| 2002/0116049 A1* | 8/2002 | Girton et al. | 623/1.15 |
| 2002/0120322 A1 | 8/2002 | Thompson et al. | 623/1.11 |
| 2003/0055485 A1* | 3/2003 | Lee et al. | 623/1.15 |
| 2003/0195606 A1 | 10/2003 | Davidson et al. | |
| 2004/0073291 A1 | 4/2004 | Brown et al. | 623/1.15 |
| 2004/0117002 A1 | 6/2004 | Girton et al. | |
| 2007/0219624 A1 | 9/2007 | Brown et al. | |

* cited by examiner

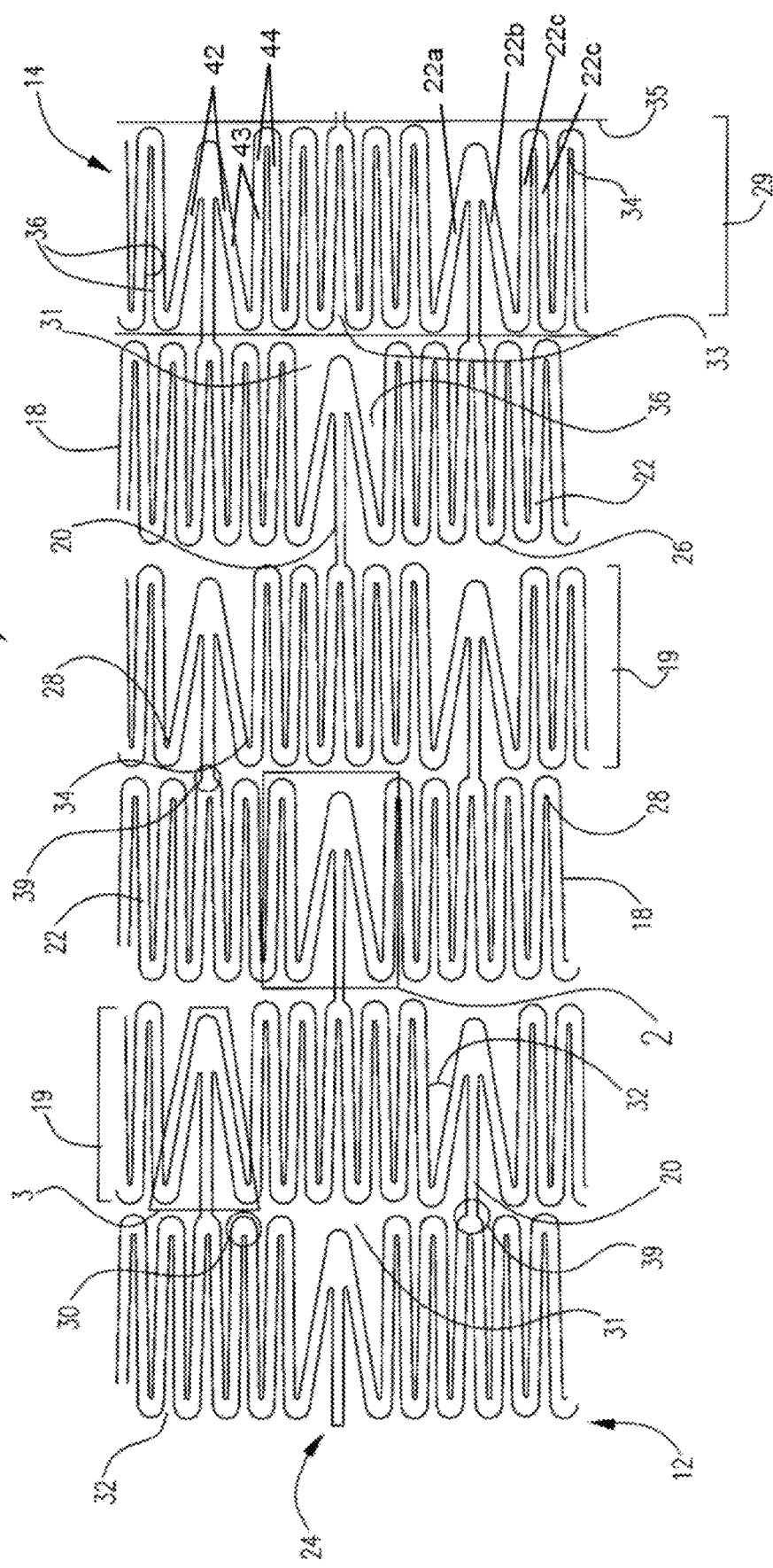

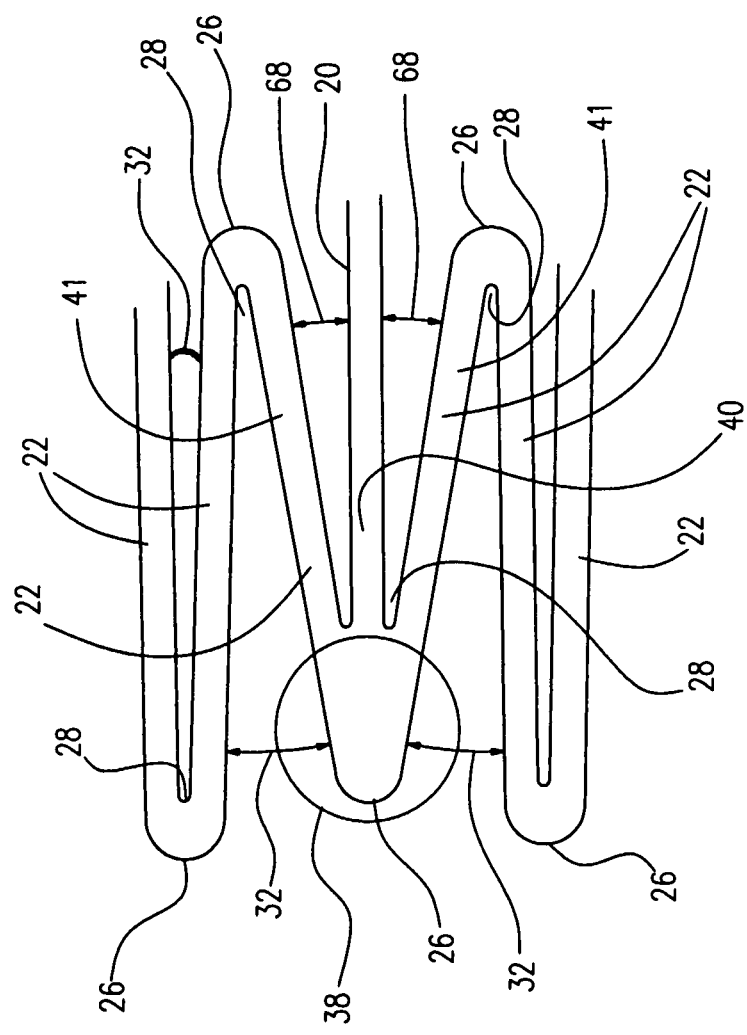

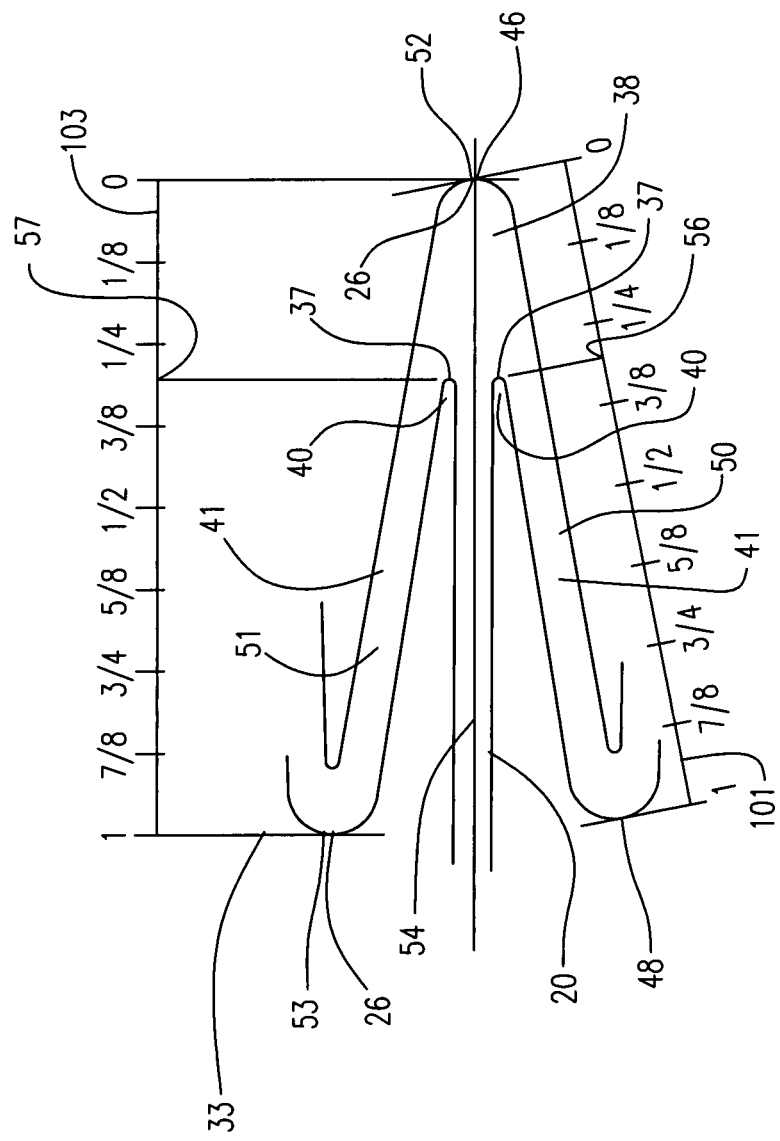

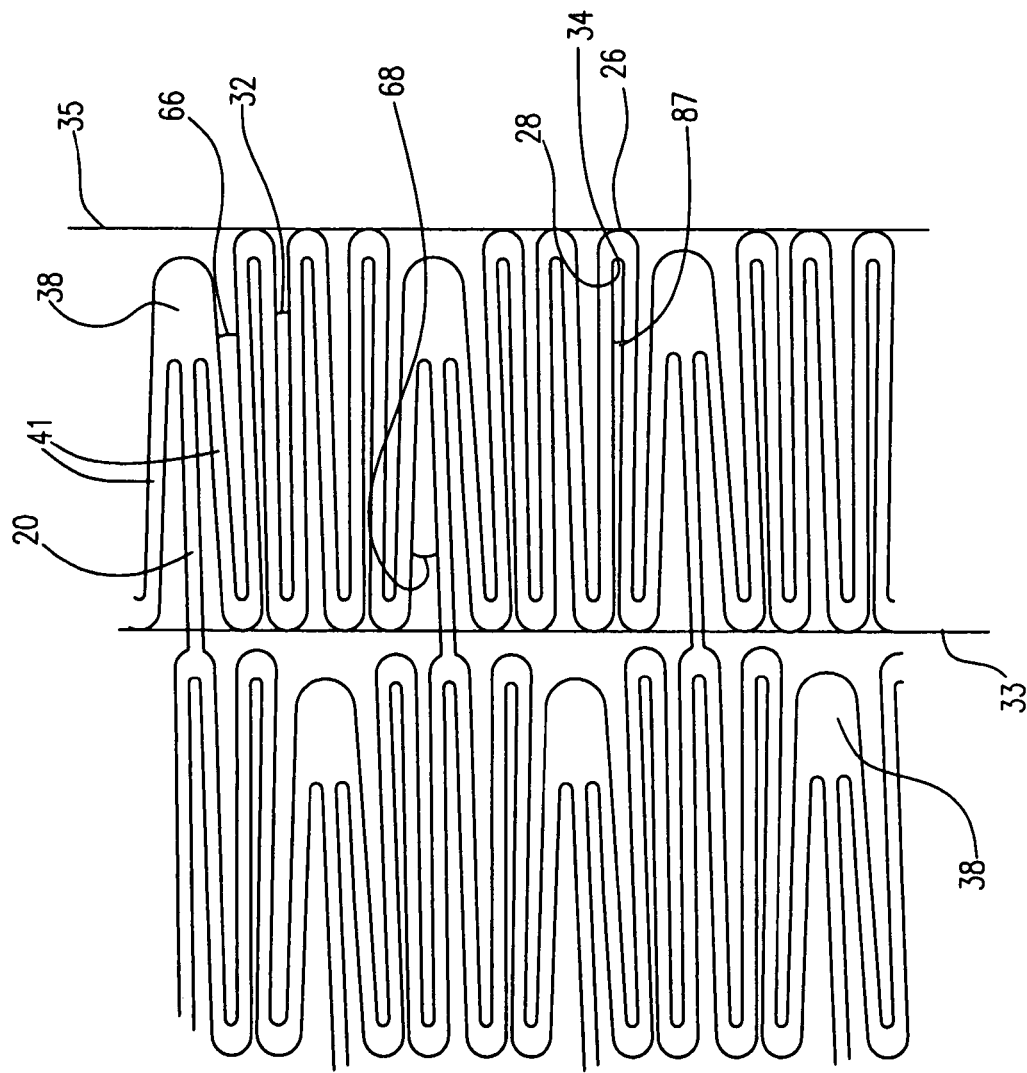

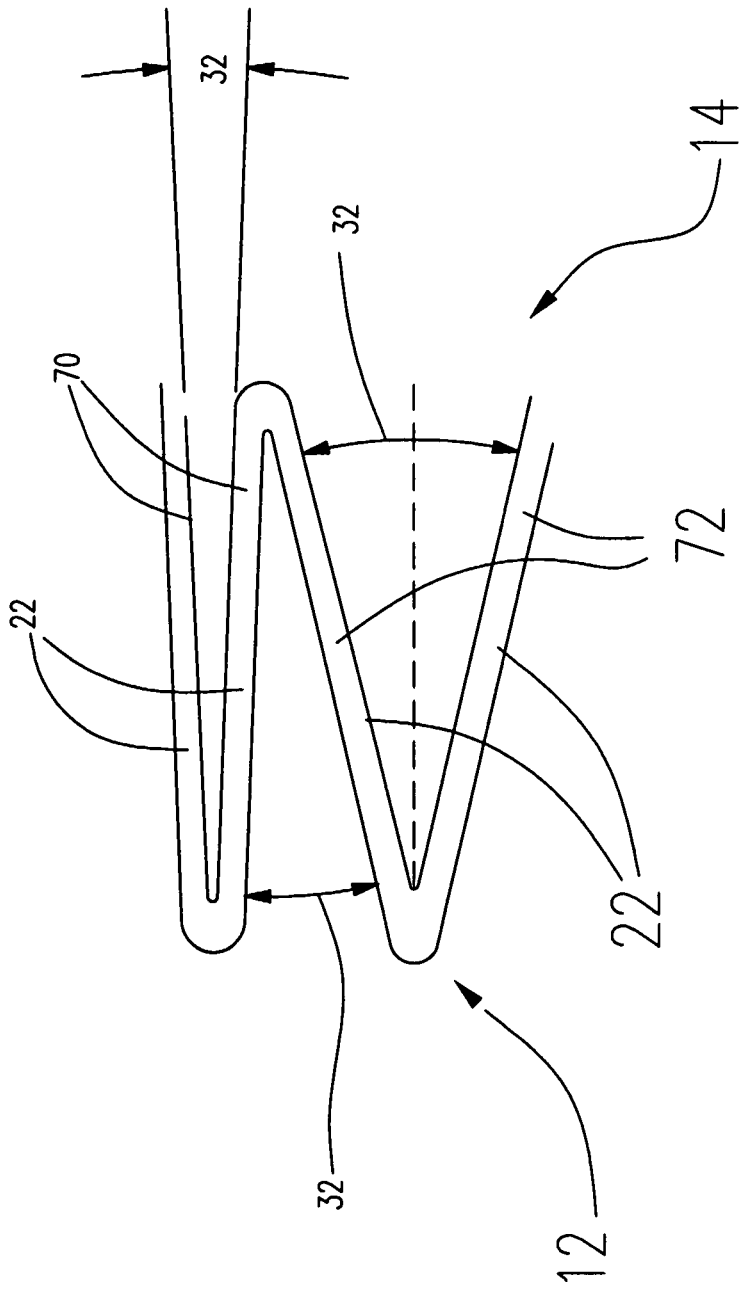

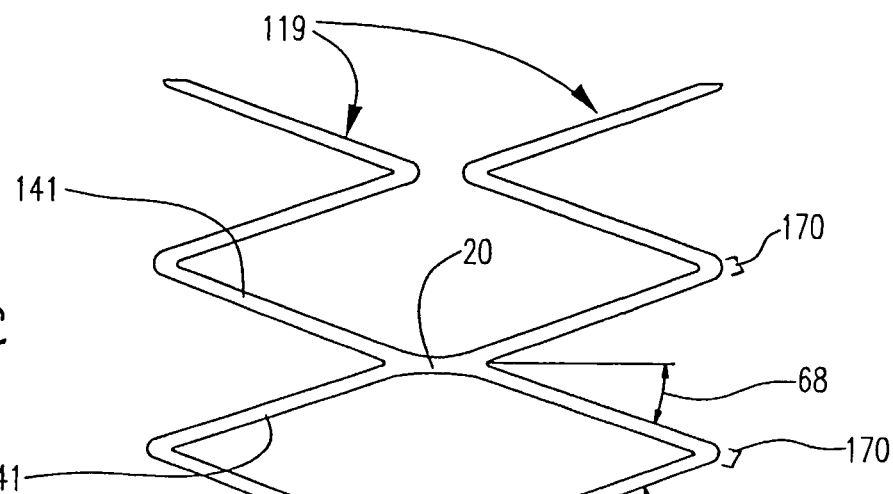
FIG. 9C
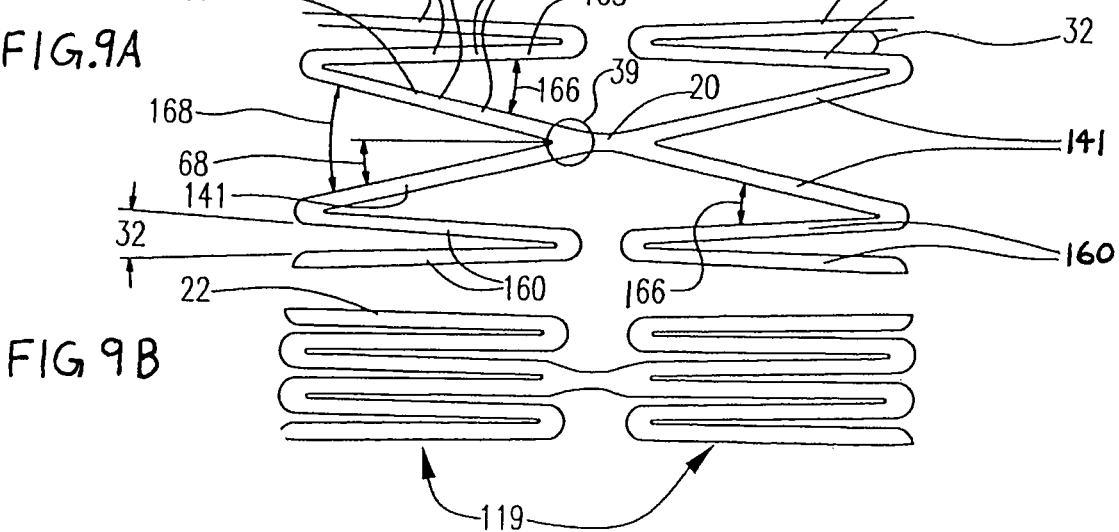
FIG. 9A
FIG. 9B

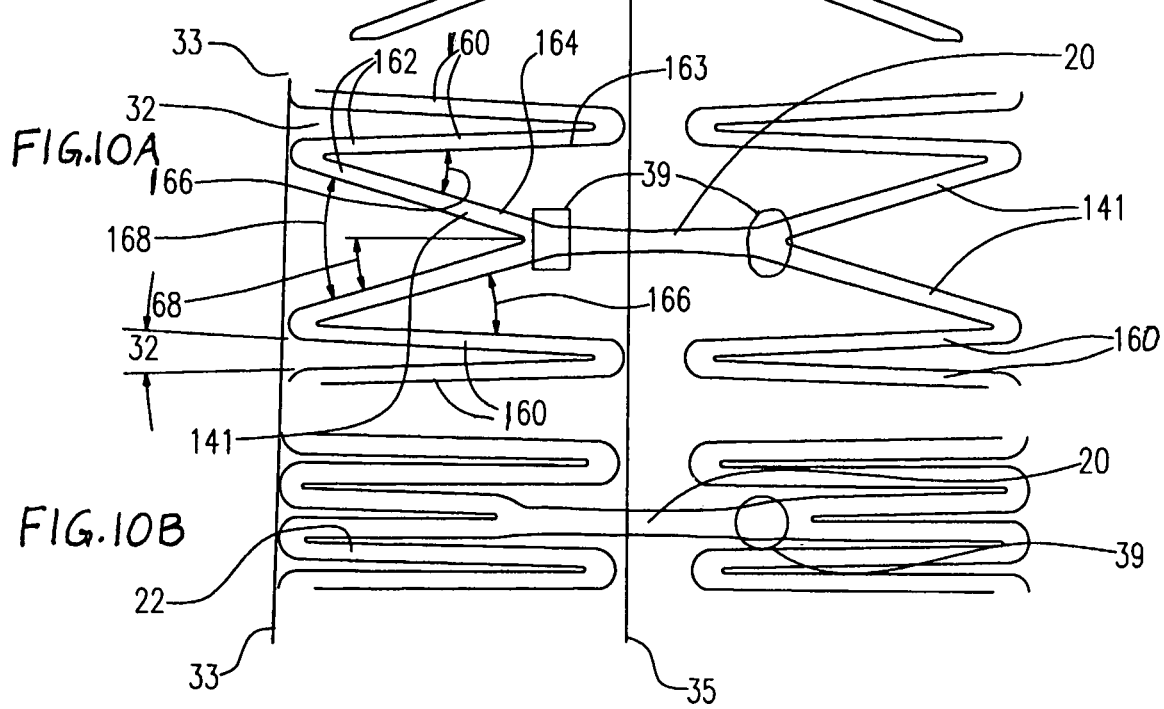

STENT DESIGN WITH STRUTS OF VARIOUS ANGLES AND STIFFNESS

FIELD OF THE INVENTION

This invention relates to implantable medical devices, such as stents, their manufacture, delivery and methods of use.

BACKGROUND OF THE INVENTION

A stent is a medical device introduced into a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable). An example of a balloon expandable stent is shown in U.S. Pat. No. 5,843,120. An example of a self-expanding stent is described in WO 96/26689.

Stents may be created by methods including cutting or etching a design from a tubular stock, from a flat sheet which is cut or etched and which is subsequently rolled or from one or more interwoven wires or braids.

There remains a need for stent patterns that provide proper scaffolding support and drug delivery in the expanded state, while also allowing for crimpability and for flexibility and deliverability in the unexpanded state.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

The present invention is directed toward stents and the manipulation of stent strut lengths, widths and strut pair angles to achieve a stent that has similar strut pair angles in the stent's expanded state. In some embodiments, the present invention is directed toward a stent having a plurality of axially spaced serpentine bands, each serpentine band having an axis circumferentially oriented around the longitudinal axis of the stent. The serpentine bands have a plurality of struts spaced along the axis of the serpentine band forming alternating peaks and valleys. The serpentine bands are interconnected via a plurality of interconnecting struts to form a plurality of cells defined by axially adjacent serpentine bands and circumferentially adjacent interconnecting struts. In some embodiments, the struts vary in stiffness and form angles that, with respect to the horizontal, are all similar at the expanded deployed diameter of the stent and at the crimped diameter of the stent, but are different at the as-cut diameter and through stent expansion.

In some embodiments, the stent has a plurality of interconnecting struts axially connecting the serpentine bands and a plurality of connector nodes, wherein an interconnecting strut and the first ends of a first and second strut of an adjacent pair of struts converge to form each connector node. Within at least one of the serpentine bands and up to all of the serpentine band, the stent has a plurality of first and second struts that are associated with a connector node that have a greater stiffness than a plurality of struts that are not associated with a connector node. In some embodiments, the first and second struts that are associated with a connector node are associated with a peak connector node and in some embodiments they are associated with a valley connector node.

In some embodiments, the stent has a plurality of axially spaced serpentine bands. Each serpentine band comprises a plurality of struts, wherein adjacent struts are connected to each other forming a plurality of peaks and valleys. The plurality of struts comprise a plurality of adjacent pairs of struts, wherein each adjacent pair of struts comprises a first strut and a second strut and wherein the first and second struts have a first end, a second end and a length. A plurality of interconnecting struts axially connects the serpentine bands. The stent further includes a plurality of valley connector nodes, wherein an interconnecting strut and the first ends of a first and second strut of an adjacent pair of struts converge to form the valley connector nodes. At a point where the interconnecting strut and the first ends of a first and second strut of an adjacent pair of struts converge, the plurality of valley connector nodes have a circumferential width that is at least the combined width of the interconnecting strut and the first and second struts of the adjacent pair of struts and extend axially to form a peak.

In some embodiments, the stent is characterized in that a first node valley is formed between a first strut and the interconnecting strut and a second node valley is formed between a second strut and the interconnecting strut. The first and second node valleys each have a bottom center point, wherein the bottom center point of the first node valley is at a point that is between 3/16 and 1/2 of the length of the first strut from its first end to its second end and the bottom center point of the second node valley is at a point that is between 3/16 and 1/2 of the length of the second strut from its first end to its second end. In some embodiments, the bottom center points of the node valleys are at points that are between 1/4 and 7/16 of the length of the respective struts. In some embodiments, the bottom center points of the node valleys are at points that are between 1/4 and 3/8 of the length of the respective struts. In some embodiments, the bottom center points of the node valleys are at points that are about 5/16 of the length of the respective struts.

In some embodiments, pluralities of first and second struts that are associated with a valley connector node are shorter than a plurality of struts that are not associated with a valley connector node. In some embodiments, pluralities of first and second struts that are associated with a peak connector node are shorter than a plurality of struts that are not associated with a peak connector node.

In some embodiments, within at least one up to all of the serpentine bands, a plurality of first and second struts that are associated with a peak or valley connector node have a greater girth than a plurality of struts that are not associated with a connector node. In some embodiments, within at least one up to all of the serpentine bands, a plurality of first and second struts that are associated with a peak or valley connector node have a greater width than a plurality of struts that are not associated with a connector node.

In some embodiments, the valley connector nodes have a constant curvature from the first strut to the second strut.

In some embodiments, the stent comprises a plurality of strut pair opening angles formed by the first and second struts of adjacent pairs of struts. The plurality of strut pair opening angles comprise a plurality of first opening angles and a plurality of second opening angles, wherein the first and second opening angles all face the same direction relative to the longitudinal axis of the stent. When the stent is in its as-cut state, the first opening angles are larger than the second opening angles. In some embodiments, when the stent is in its as-cut state, the first opening angles are twice as large as the second opening angles. In some embodiments, the first opening angles are formed by a strut that is associated with a valley connector node and a strut that is not associated with a valley connector node.

In some embodiments, the stent further comprises a plurality of node approach opening angles, each being formed by a strut and an interconnecting strut that are associated with the same valley connector node. When the stent is in its as-cut state, the node approach opening angles are larger than the second opening angles. When the stent is in its crimped state, the first opening angles are substantially similar to the second opening angles and, when the stent is in its expanded state, the first opening angles are substantially similar to the second opening angles.

In some embodiments, the serpentine bands further comprise strut pair opening angles formed by the first and second struts of the adjacent pairs of struts. The plurality of strut pair opening angles comprise a plurality of first opening angles and a plurality of second opening angles, wherein the first and second opening angles all face the same direction relative to the longitudinal axis of the stent and wherein, when the stent is in its as-cut state, the first opening angles are larger than the second opening angles and, when the stent is in its crimped state, the first opening angles are substantially similar to the second opening angles. In some embodiments, the first opening angles are formed by a strut that is associated with a valley connector node and a strut that is not associated with a valley connector node.

In some embodiments, at least a portion of the stent is configured to include one or more mechanisms for the delivery of a therapeutic agent. Often the agent will be in the form of a coating or other layer (or layers) of material placed on a surface region of the stent and is adapted to be released at the site of the stent's implantation or areas adjacent thereto. The therapeutic and/or polymeric coatings may comprise one or more non-genetic therapeutic agents, genetic materials and cells and combinations thereof.

In some embodiments, an embodiment of the inventive stent is mounted on a stent delivery catheter. The present invention also further includes methods of delivering the disclosed inventive stents to a target site in a bodily vessel.

In some aspects, the present invention allows for unique patterns requiring a larger strut opening for laser cutting without compromising the stent uniformity in a targeted vessel. It also allows for preferential strut bending. The bending deflection is proportional to the strut stiffness. With preferential strut bending, the bending strain may be localized to specific areas that might be under differing external forces.

In some aspects, the present invention improves the crimped diameter profile by offsetting the strut intersection nodes, for example in stents with peak-to-valley connectors.

In some aspects, the present invention allows for an immobile strut. The use of immobile struts may be an advantage for a stent with a mid-strut connector or any other junction that needs to be relatively static throughout stent expansion stages.

These and other embodiments that characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described an embodiments of the invention.

BRIEF DESCRIPTION OF THE DRAWINGS

A detailed description of the invention is hereafter described with specific reference being made to the drawings.

FIG. 1 is a side view of an embodiment of the invention.

FIG. 2 is a fragmentary enlargement of portion 2 of the stent of FIG. 1.

FIG. 3 is a fragmentary enlargement of portion 3 of FIG. 1.

FIG. 6A is a partial side view of the stent shown in FIG. 1 in its crimped configuration.

FIGS. 7A-C are partial side views of an embodiment of the invention.

FIG. 9A is a partial side view of an embodiment of the invention in its as-cut configuration.

FIG. 9B is a partial side view of the stent shown in FIG. 9A in its crimped configuration.

FIG. 9C is a partial side view of the stent shown in FIGS. 9A and 9B in its expanded or deployed configuration.

FIG. 10A is a partial side view of an embodiment of the invention in its as-cut configuration.

FIG. 10B is a partial side view of the stent shown in FIG. 10A in its crimped configuration.

FIG. 10C is a partial side view of the stent shown in FIGS. 10A and 10B in its expanded or deployed configuration.

DETAILED DESCRIPTION OF THE INVENTION

Figure 4A:
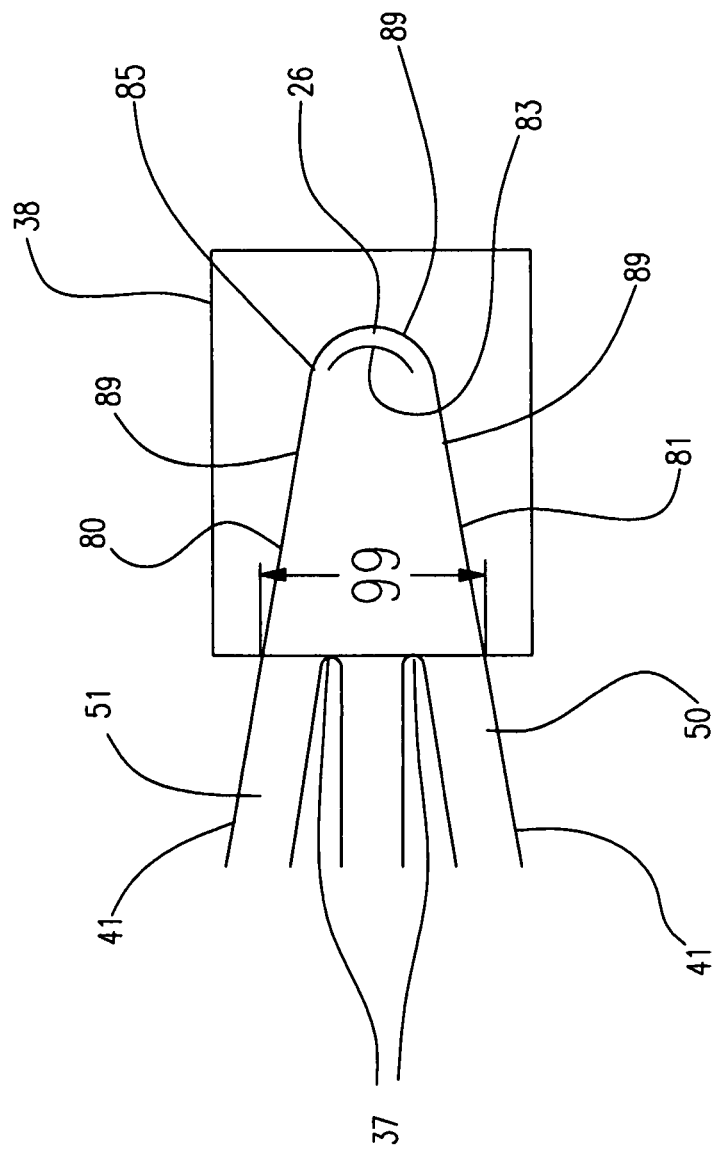
FIGS. 4A and 4B are further fragmentary detail views of the node shown in FIG. 3.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the Figures shall refer to like features unless otherwise indicated.

Depicted in the figures are various aspects of the invention. Elements depicted in one figure may be combined with, or substituted for, elements depicted in another Figure as desired.

In one embodiment, as shown in FIG. 1, the invention is directed to a stent, shown generally at 10, having a proximal end 12 and a distal end 14, and comprising a plurality of axially spaced serpentine bands 18. Each serpentine band 18 is shaped in a tubular form forming a plurality of expansion columns 19. Each serpentine band 18, and therefore each expansion column 19, is connected to a longitudinally adjacent serpentine band 18 via a plurality of interconnecting struts 20. The interconnecting struts shown are of substantially the same length and arranged in a uniform manner. However, it should be understood that the interconnecting struts 20 may vary in number, length and pattern.

A plurality of cells 31 are defined by longitudinally adjacent serpentine bands 18 and circumferentially adjacent interconnecting struts 20. It should be understood that the shape of the cells vary and the cell pattern may be uniform or irregular.

The serpentine bands 18 comprise struts 22 circumferentially arranged around the longitudinal axis 24 of the stent 10. Adjacent struts 22 are connected to one another forming alternating peaks 26 and valleys 28. Since the junctures 30 between adjacent struts 22 could be considered to form a peak 26 and a valley 28 from a top view, the alternating peaks 26 and valleys 28 characteristic should be considered from a proximal end 12 to a distal end 14 or a distal end 14 to a proximal end 12 perspective. Each expansion column 19 has a proximal circumferential perimeter 33 defined by its proximal peaks 26 and a distal circumferential perimeter 35 defined by its distal peaks 26. The circumferential perimeters 33, 35, define the width 29 of the expansion column 19. It should be understood that the present invention contemplates other generally serpentine configurations and not just the exact configuration shown. As shown in FIG. 1, struts 22 include struts 22a, 22b and 22c. Struts 22a and 22b are connected to each other by a juncture 30 to form a first pair of struts 42. Struts 22b and 22c are connected to each other by a juncture 30 to form a second pair of struts 43. A third pair of struts 44 is formed where two struts 22c are connected to each other by a juncture 30.

Adjacent strut 22 pairs that are directly connected to each other form a strut pair opening angle 32, wherein the valley 28 center point 34 is the vertex or low point in the valley 28 and the inner sides 36 of the strut 22 pair are the sides of the strut pair opening angle 32. The stent 10 has an as-cut condition, as shown in FIG. 1, a crimped or contracted condition and an expanded condition. The as-cut condition is the design and size of the stent 10 when it is cut from a tube. Cutting stent designs from a tube is well known in the art and is typically done via laser cutting. From this as-cut condition, the stent 10 may be crimped down to a crimped or contracted condition, which has a smaller diameter than the as-cut condition, decreasing the strut pair opening angles 32. The crimped or contracted stent may further be expanded to an expanded condition, increasing the strut pair opening angles 32. When the stent 10 is expanded, the diameters of the expansion columns 19 increase, the distance between circumferentially adjacent peaks 26 increases and the valleys become more obtuse.

FIG. 2 is an enlarged view of a portion 2 of the stent of FIG. 1. As can be seen from this illustration of a portion of an as-cut serpentine band 18, the serpentine bands 18 further include valley connector nodes 38. A valley connector node 38 is the juncture between an adjacent pair of struts 41 (22) that form a peak 26 and an interconnecting strut 20, which splits a pair of node valleys 40 (28) between the adjacent pair of struts 41.

Examples of peak connector nodes 39 can be seen in FIG. 1. A peak connector node 39 is the juncture between a peak 26 formed by connected adjacent struts 22 and an interconnecting strut 20.

FIG. 3, which is an enlarged view of a portion 3 of the stent 10, shows a valley connector node 38. The bottom center points 37 (34) of the pair of node valleys 40 are the low points in the node valleys 40 formed between the adjacent pair of struts 41 and the interconnecting strut 20. In the embodiment shown, the center points 37 of the pair of node valleys 40 that are associated with the valley connector node 38 are interiorly positioned in the expansion column 19 relative to the proximal circumferential perimeter 33 and the distal circumferential perimeter 35 and relative to the valley center points that are not associated with a valley connector node 38. The portion of struts 41 that are immediately adjacent to the bottom center points 37 are considered to be a close approximation of the yield point of the strut 41 upon contraction and expansion of the stent 10.

Portions of the stent 10 that are "associated with the valley connector node 38" means those portions that define the valley connector node 38. As will be discussed below with regard to peak connectors, "associated with a peak connector node 39" means those portions that define the peak connector node 39. The valley connector node 38 extends from the valley center points 37 of the pair of node valleys 40 to the peak 26 of the juncture of the pair of adjacent struts 41 and the interconnecting strut 20.

FIG. 4A illustrates the perimeter of the valley connector node 38. As shown, the perimeter extends between valley center points 37, perpendicularly across the pair of struts 41 and up to the peak 26. At the point where the interconnecting strut 20 and the pair of adjacent struts 41 converge, the valley connector node 38 has a circumferential width 99 that is at least the combined width of the interconnecting strut 38 and the adjacent pair of struts 41. The valley connector node 38 extends axially. In the embodiment shown, the valley connector node 38 decreases in width to the peak 26. In some embodiments, the circumferential width of the valley connector node 38 may vary from the point of convergence 99 to the peak 26. The peak 26 may be rounded in some embodiments and flattened in some embodiments. It should be understood that, in some embodiments, the valley center points 37 may not be circumferentially aligned. One may be distal or proximal relative to the axis 24 of the stent 10 to the other.

Figure 4B:
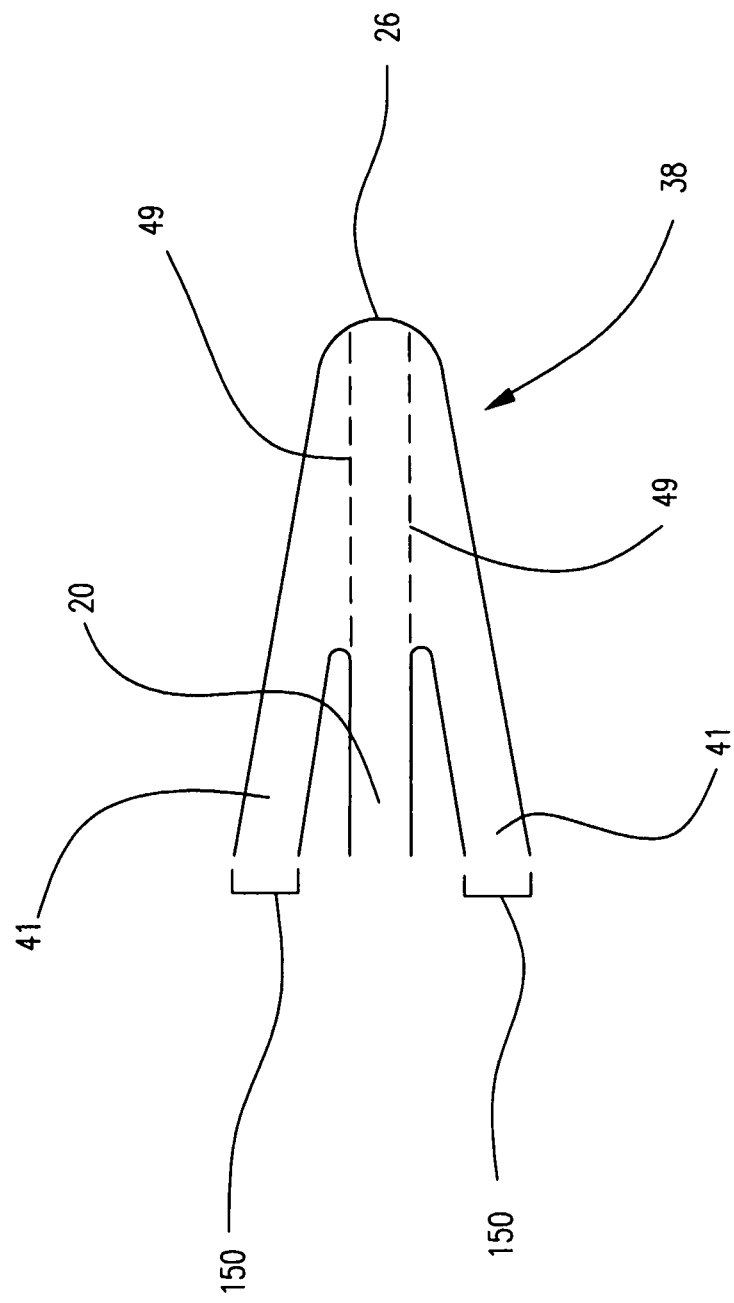

Another way of looking at the shape of the valley connector node 38 of an embodiment of the invention is illustrated in FIG. 4B. The dotted lines 49 represent the projected extension of the interconnecting strut 20 within the valley connector node 38. With this extension, the adjacent struts 41 appear to be beveled at the ends to conform to the sides of the extension of the interconnecting strut 20 to give a triangular appearance. As mentioned above, the node approach opening angle 68 may vary in the as-cut state. The peak 26 may be rounded in some embodiments and flattened in some embodiments.

In some embodiments, the peak 26 of the valley connector node 38 formed by the pair of struts 41 has an outer edge 89 constant curvature 83 from an outer side 80 of a first strut 51 to an outer side 81 of a second strut 50. What is meant by constant curvature is that the curvature of the outer edge 85 of the node 38 constantly increases or positively increases from the outer side 80 to a high point and then constantly decreases or positively decreases to the outer side 81.

For the purposes of locating the interior positioning of the bottom center points 37 of the pair of node valleys 40, rulers 101, 103, are shown in FIG. 3. Ruler 101 extends from a first end 46 associated with the valley connector node 38 of a first strut 50 to a second end 48 of the first strut 50. This is considered to be the length of the strut 50. The ruler 101 is position parallel with the first strut 50. A ruler 103 is also shown extending from a first end 52 of a second strut 51 to a second end 53 of the second strut 51. The ruler 103 is position parallel with a center line 54 of the interconnecting strut 20 associated with the valley connector node 38 extending from the peak 26 associated with the valley connector node 38 to the proximal circumferential perimeter 33 of the expansion column 19. Instead of the proximal circumferential perimeter 33, a line from the peak 26 of the second end 53 of the second strut 51 to the peak 26 of the second end 48 of the first strut 50 may also be used. It should be understood that the center line 54 may extend to the distal circumferential perimeter 35 in a mirror image representation. Either measure may be used on either of the first 50 or second 51 struts.

Both rulers 101, 103, are squared off at the ends 46, 48, 52, 53, of the measured struts 50, 51. The rulers 101, 103, start at 0 and go to 1, which indicates the complete length. The intermediate hashes are proportional measurements. For example, in ruler 101, the length of strut between 0 and ½ indicates the first or beginning half of the strut and, similarly, the length of strut between ½ and 1 indicates the second or last half of the strut. Similarly, in ruler 103, the length of center line 54 of the interconnecting strut 20 between 0 and ½ indicates the first or beginning half of the center line 54 and, similarly, the length of the center line 54 between ½ and 1 indicates the second or last half of the center line 54.

In the embodiment shown, using the ruler 101, taking a line 56 perpendicular to the ruler 101 from the valley center point 37, it is shown that the valley center point 37 is at about the 5/16 mark. As such, it can be said that the valley center point 37 is at a point that is 5/16 of the length of the first strut 50 from its first end 46 to its second end 48. In some embodiments, the valley center point 37 is at or between the ⅛ mark and the ⅜ mark. In some embodiments, the valley center point 37 is at or between the ¼ mark and the ⅜ mark.

Ruler 103 may also be used in determining the positioning of the bottom valley center points 37. In the embodiment shown, using the ruler 103, taking a line 57 perpendicular to the center line 54 of the interconnecting strut 20 and ruler 103 from the valley center points 37, it is shown that the valley center point 37 is at about the 5/16 mark. As such, it can be said that the valley center point 37 is at a point that is 5/16 of the length of the interconnecting strut 20 from the peak 26 of the valley connector node 38 to the proximal circumferential perimeter 33. In some embodiments, the valley center point 37 is at or between the ⅛ mark and the ⅜ mark. In some embodiments, the valley center point 37 is at or between the ¼ mark and the ⅜ mark.

Figure 5:
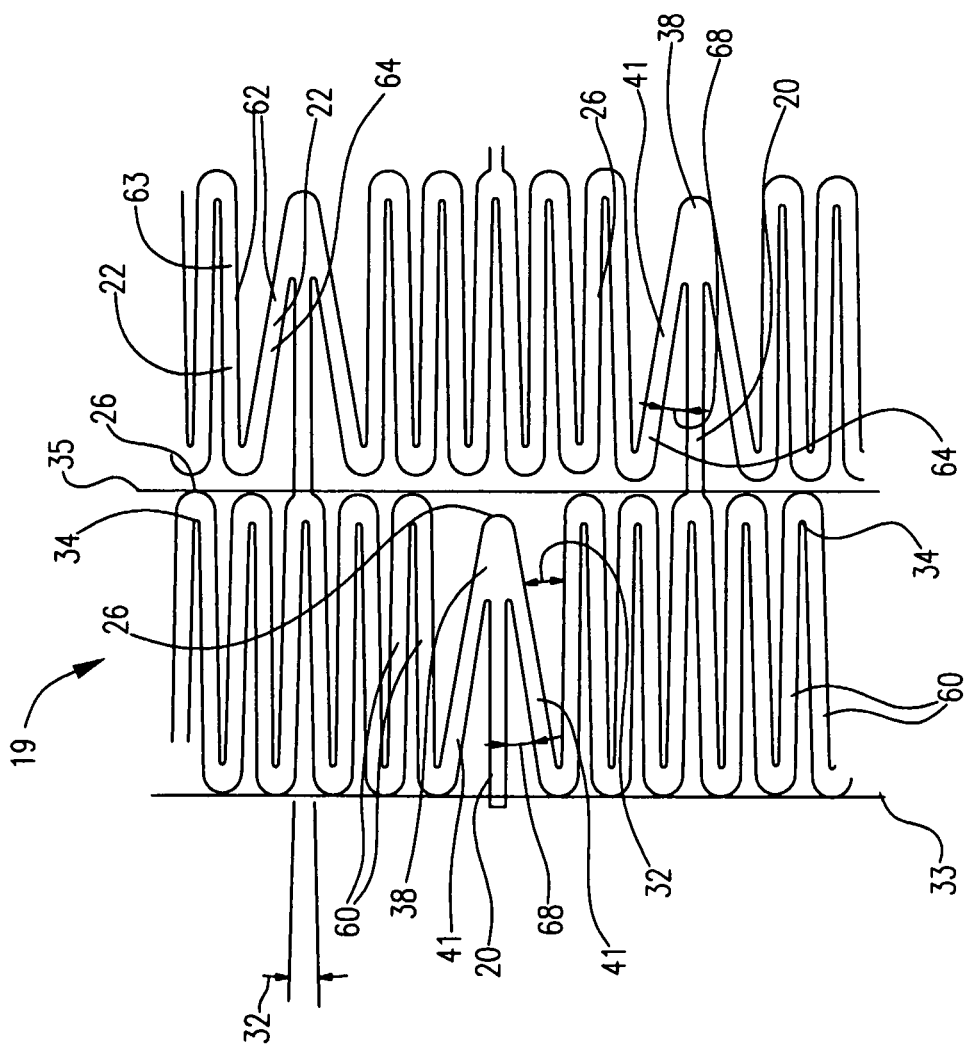
FIG. 5 is a partial side view of the stent shown in FIG. 1 in its as-cut configuration.

Turning now to FIG. 5, which is a fragmentary view of the stent of FIG. 1 showing portions of the adjacent serpentine bands 19 in their as-cut configuration. As can be seen, in some embodiments, the peak 26 of the valley connector nodes 38 are interiorly positioned in the expansion column 19 relative to the proximal circumferential perimeter 33 and the distal circumferential perimeter 35 and relative to the peaks 26 of adjacent strut pairs 60 that are not associated with a valley connector node 38. In other words, the distance between a peak 26 of an adjacent strut pair 60 that is not associated with a valley connector node 38 and the proximal circumferential perimeter 33 is greater than the distance between a peak 26 of a valley connector nodes 38 and the proximal circumferential perimeter 33. In some embodiments, the peak of the valley connector node 38 is substantially aligned with the distal circumferential perimeter 35. In some embodiments, the struts of strut pair 41 may be 75%-100% of the length of the struts of strut pair 60.

Figure 8A:
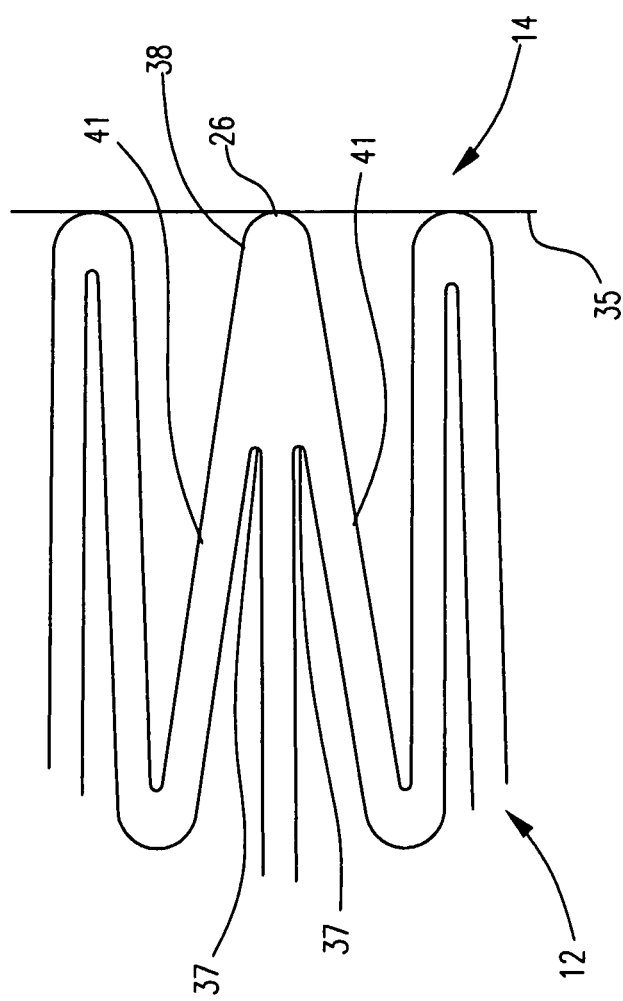
FIGS. 8A-C are partial side views of an embodiment of the invention.
Figure 8B:
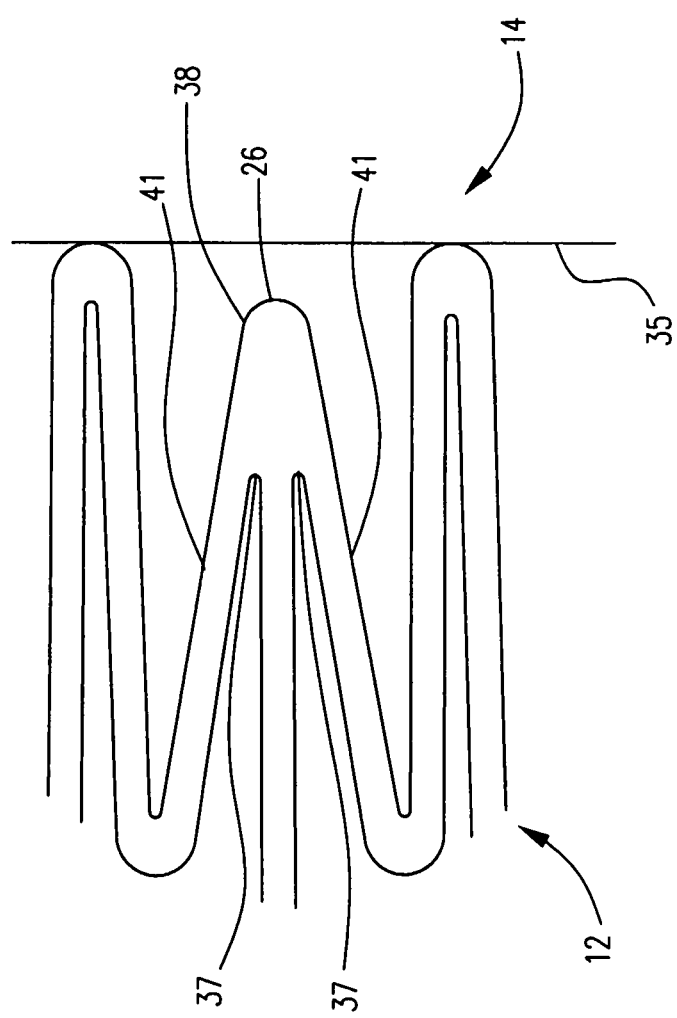
Figure 8C:
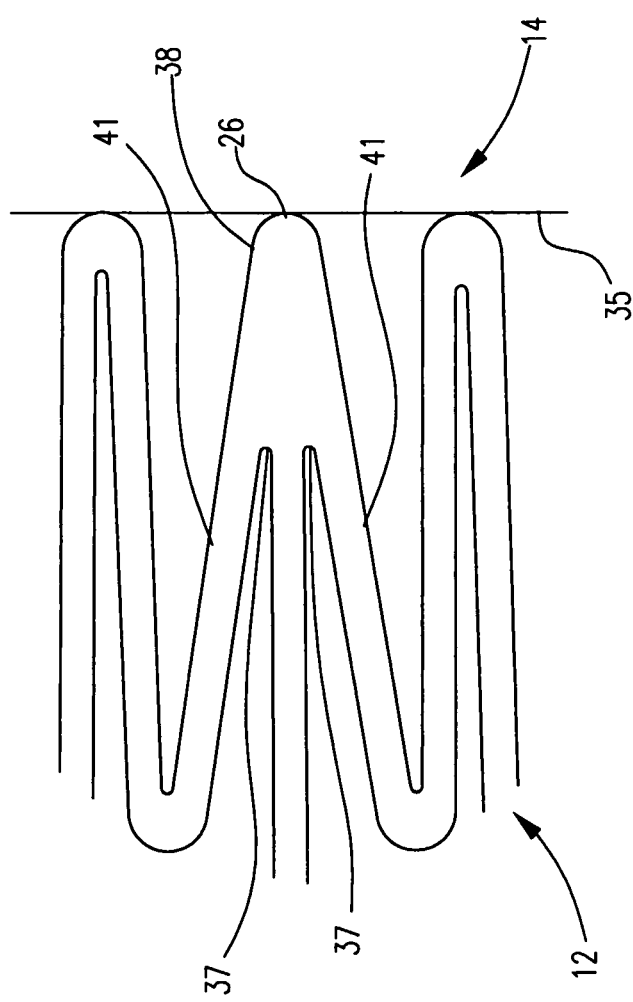

The size and stiffness of the valley connector node 38 may be varied by varying either or both the axial positioning of the peak 26 of the valley connector node 38 and the axial positioning of the bottom valley center points 37 of the valley connector node 38. Non-limiting examples of differing configurations are illustrated in FIGS. 8A-C. In FIG. 8A, the peak 26 of the node 38 is substantially aligned with the distal circumferential perimeter 35. The embodiment shown in FIG. 8B differs in that the peak 26 of the node 38 is moved proximally or interiorly. The embodiments shown in FIG. 8C differs from the one shown in FIG. 8A in that the bottom valley center points 37 are moved proximally or interiorly. By adding material into the inside instead of the outside allows for better crimpability. Moving center points 37 inward and away from perimeter 35 also allows for a lower crimped profile. Altering the node 38 allows one to manipulate the stress around the node 38. The different length struts open up to similar angles, but have differing stiffness.

In the as-cut configuration, as shown in FIG. 5, the strut pair opening angles 32 of adjacent strut pairs 60 that are not associated with a valley connector node 38 are substantially uniform. In some embodiments, in a particular expansion column 19, an adjacent strut pair 62 that includes one strut 63 that is not associated with a valley connector node 38 and one strut 64 that is associated with a valley connector node 38 forms a node strut pair opening angle 66 that is larger than those formed by adjacent strut pairs 60 that are not associated with a valley connector node 38. In some embodiments, angle 68 may be up to four times the size of angle 32. Angle 66 is a function of angles 68 and 32. It 66 is about equal to the size of angle 68 plus one half the size of angle 32. The size of angle 66 may be up to 4.5 times the size of angle 32.

It should be understood that in some embodiments there may be some strut pair opening angles 32 that are as large as or larger than at least some or all of the node strut pair opening angles 66. In some embodiments, at least some or all of the node strut pair angles 66 are larger than a majority of the non-node associated strut pair opening angles 32. For instance, the node strut pair angles 66 may be larger than ⅔ of the non-node associated strut pair opening angles 32, larger than at least ¾ of the non-node associated strut pair opening angles 32, or larger than all of the non-node associated strut pair opening angles 32.

In some embodiments, in a particular as-cut expansion column 19, as shown in FIG. 5, a node approach opening angle 68 is formed by one strut 64 that is associated with a valley connector node 38 and an interconnecting strut 20 that is larger than those formed by adjacent strut pairs 60 that are not associated with a valley connector node 38. It should be understood that in some embodiments there may be some strut pair opening angles 32 that are as large as or larger than at least some or all of the node approach opening angles 68. In some embodiments, at least some or all of the node approach opening angles 68 are larger than a majority of the non-node associated strut pair opening angles 32. For instance, the node approach opening angles 68 may be larger than at least ⅔ of the non-node associated strut pair opening angles 32, larger than ¾ of the non-node associated strut pair opening angles 32, or larger than all of the non-node associated strut pair opening angles 32.

FIG. 6A illustrates the portion of a stent 10 shown in FIG. 5 crimped down into a contracted configuration. As can be seen, the differences between the non-node associated opening angles 32 and the node strut pair angles 66 and the node approach opening angles 68 are decreased to a point where they all are essentially closed. Due to crimping, the struts 22 may be curved and warped such that the angles produced are essentially zero. The curvature of the peaks 26 and valleys 28 are also such that they resist further crimping around the valley center point 34 resulting in what appears to be negative angles 87.

Figure 6B:
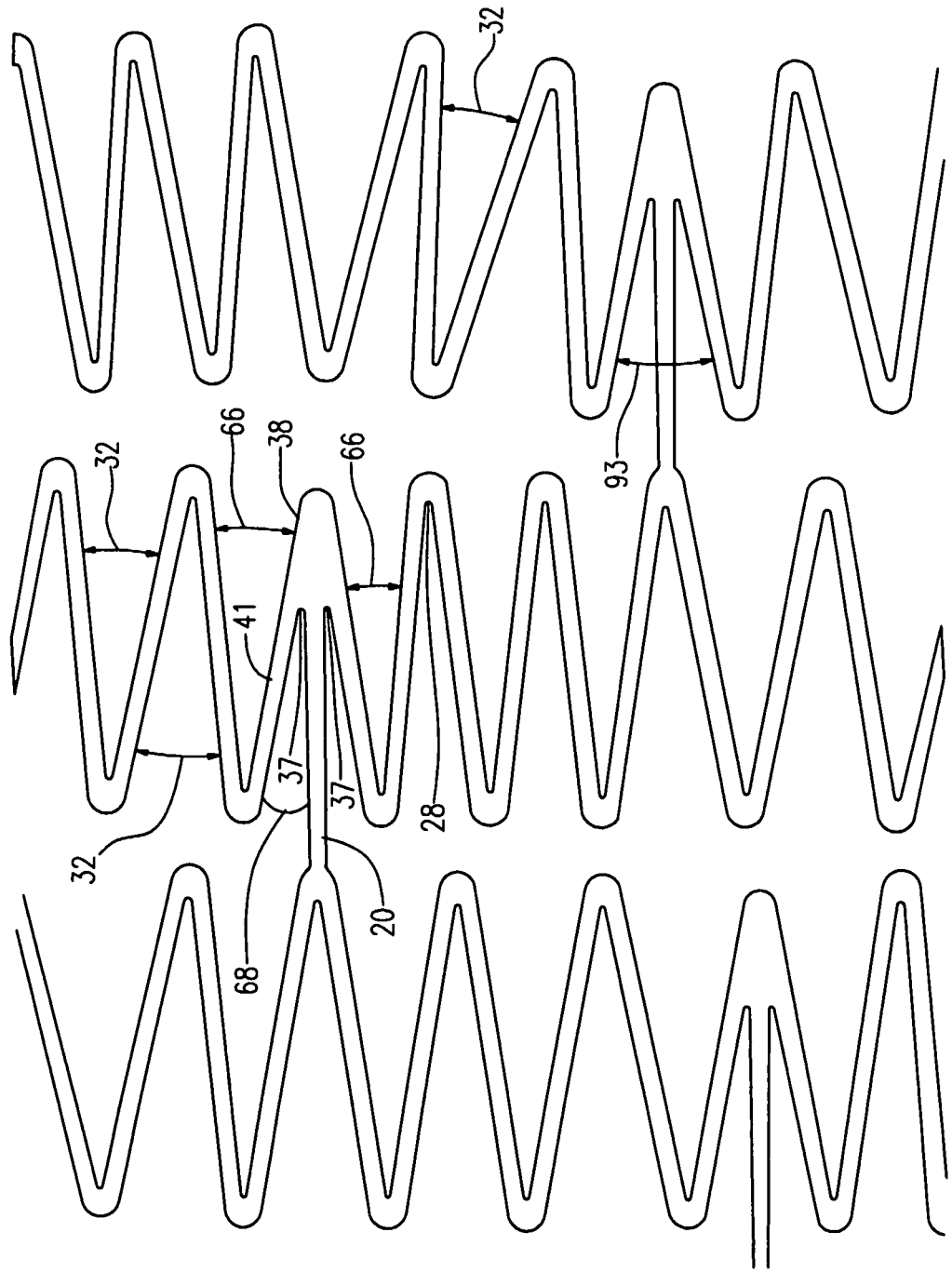
FIG. 6B is a partial side view of the stent shown in FIG. 1 in its expanded or deployed configuration.

FIG. 6B illustrates the portion of a stent 10 shown in FIG. 5 expanded to its deployed configuration. This expansion is achieved through self-expansion, such as with self-expanding stents, or through forced expansion, such as with a balloon. As can be seen, in this configuration, the differences between the non-node associated opening angles 32 and the node strut pair angles 66 are substantially similar. Also, as can be seen, the angle 93, which is a combination of the angles 68 formed between the adjacent pair of struts 41 and the interconnecting strut 20 is substantially similar to angles 66 and 32 in the expanded configuration.

Figure 7B:
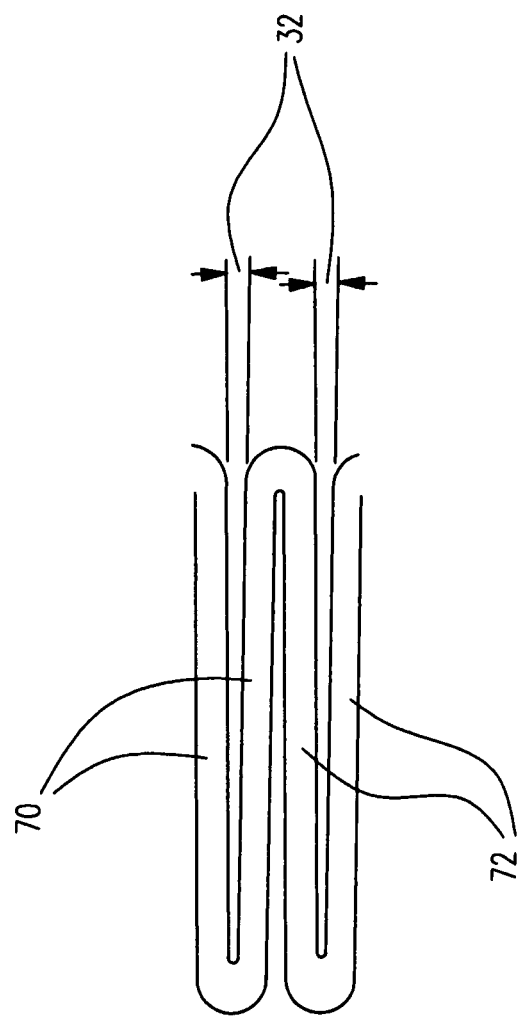
Figure 7C:
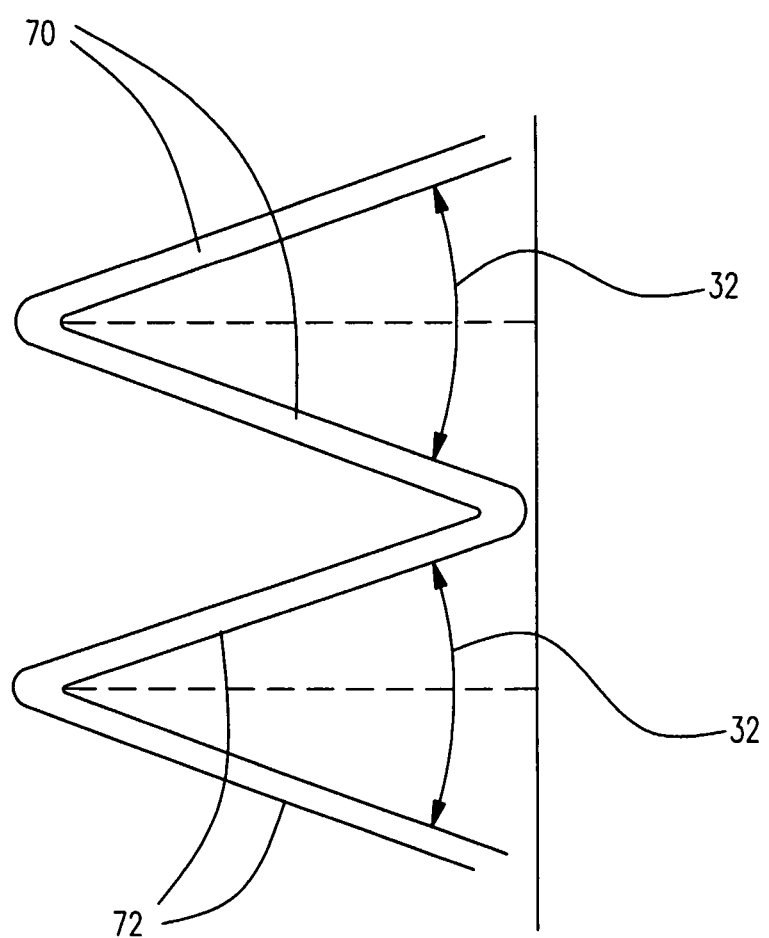

Turning now to FIGS. 7A-C, in some embodiments of the invention, regardless of the configuration of interconnecting struts 20 and the presence of connector nodes 38, 39, the strut pair opening angles 32 may vary or be non-uniform in a particular expansion column 19 in the stent's 10 as-cut configuration. If valley connector nodes 38 are present, the non-uniformity of strut pair opening angles 32 may apply to non-node associated adjacent strut pairs.

FIG. 7A shows a portion of an expansion column 19. In this illustration, four struts 22 are shown and two adjacent strut pairs 70, 72. In describing and comparing the varying strut pair angles 32, only the angles 32 that are facing a particular direction are addressed together. In this case, the distally 14 facing angles 32 are discussed. In should be understood, a similar analysis may be done with the angles 32 facing proximally.

As can be seen in FIG. 7A, the strut pair opening angle 32 formed by adjacent strut pair 70 is smaller than the strut pair opening angle 32 formed by adjacent strut pair 72. As will be discussed, below, in some embodiments, the width of the struts that make up strut pair 72 is greater than the width of the struts that make up strut pair 70.

From the as-cut configuration shown in FIG. 7A, the stent 10 is crimped or reduced to its contracted state, as shown in FIG. 7B. As can be seen, the strut pair opening angle 32 formed by adjacent strut pair 70 is substantially similar to the strut pair opening angle 32 formed by adjacent strut pair 72. In the stent's crimped state, the strut pair opening angles 32 are essentially closed down.

From the crimped or contracted state, as shown in FIG. 7B, the stent 10 may be expanded to an expanded configuration, as shown in FIG. 7C. The expanded configuration is the configuration the stent 10 is in when it is deployed. As can be seen, the strut pair opening angle 32 formed by adjacent strut pair 70 is substantially similar to the strut pair opening angle 32 formed by adjacent strut pair 72. Although, the stent 10 is cut 7A such that there are different strut pair opening angles 32, in the crimped or contracted condition 7B and in the expanded condition 7C, the strut pair opening angles 32 are substantially similar. Upon expansion of the stent 10 from the crimped condition 7B to the expanded condition 7C, the similar strut pair opening angles 32 in FIG. 7B differentiate to a mid expansion condition, which is similar to the condition shown in FIG. 7A, and upon further expansion to the expanded condition become substantially similar again, as shown in FIG. 7C.

Turning now to FIGS. 9A-9C, in some embodiments of the invention, the manipulation of stiffness of the strut pairs 141 adjacent to an interconnecting strut 20 may also be achieved wherein the connector nodes are peak connector nodes 39. The peak connector node 39 is the juncture between an interconnecting strut 20 and strut pairs 141 adjacent to the interconnecting strut 20. These strut pairs 141 are considered to be associated with the peak connector node 39.

In the as-cut configuration, as shown in FIG. 9A, the strut pair opening angles 32 of adjacent strut pairs 160 that are not associated with a peak connector node 39 are substantially uniform. In some embodiments, in a particular expansion column 119, an adjacent strut pair 162 that includes one strut 163 that is not associated with a peak connector node 38 and one strut 164 that is associated with a peak connector node 39 forms a node strut pair opening angle 166 that is larger than those formed by adjacent strut pairs 160 that are not associated with a peak connector node 39. In some embodiments, angle 168 may be up to four times the size of angle 32. In some embodiments, angle 168 may be up to six times the size of angle 32. Angle 166 is a function of angles 168 and 32. It 166 is about equal to half the size of angle 168 plus one half the size of angle 32. The size of angle 166 may be up to 4.5 times the size of angle 32.

It should be understood that in some embodiments there may be some strut pair opening angles 32 that are as large as or larger than at least some or all of the opening angles 166. In some embodiments, at least some or all of the opening angles 166 are larger than a majority of the non-node associated strut pair opening angles 32. For instance, the opening angles 166 may be larger than ⅔ of the non-node associated strut pair opening angles 32, larger than at least ¾ of the non-node associated strut pair opening angles 32, or larger than all of the non-node associated strut pair opening angles 32.

FIG. 9B illustrates the portion of a stent shown in FIG. 9A crimped down into a contracted configuration. As can be seen, the differences between the non-node associated opening angles 32 and the angles 166, 168 associated with a peak connector node 39 are decreased to a point where they all are essentially closed. Due to crimping, the struts 22 may be curved and warped such that the angles produced are essentially zero.

FIG. 9C illustrates the portion of a stent shown in FIG. 9A and 9B expanded to its deployed configuration. This expansion is achieved through self-expansion, such as with self-expanding stents, or through forced expansion, such as with a balloon. As can be seen, in this configuration, the differences between the non-node associated opening angles 32 and the opening angles 166 and 168 are substantially similar.

Turning now to FIGS. 10A-10C, in some embodiments of the invention, the manipulation of stiffness of the strut pairs 141 adjacent to an interconnecting strut 20 may also be achieved wherein the peak connector nodes 39 are interiorly positioned in the expansion column 119 relative to the proximal circumferential perimeter 33 and the distal circumferential perimeter 35 and relative to the peaks 26 of adjacent strut pairs 160 that are not associated with a peak connector node 39. In other words, the distance between a peak 26 of an adjacent strut pair 160 that is not associated with a peak connector node 39 and the proximal circumferential perimeter 33 is greater than the distance between a peak 26 of a peak connector nodes 39 and the proximal circumferential perimeter 33.

The strut pairs 141 adjacent to an interconnecting strut 20 are shorter than the strut pairs 160 not associated with the peak connector node 39. This in turn lengthens the connector strut 20. Otherwise, the embodiment shown in FIGS. 10A-10C is the same as the embodiments shown in FIGS. 9A-9C.

In some embodiments, the peak connector node 39 is substantially aligned with the distal circumferential perimeter 35, as shown in FIG. 9A. In some embodiments, as shown in FIG. 10A, the struts of strut pair 141 may be 75%-100% of the length of the struts of strut pair 160. In some embodiments they 141 may be 75%-90% and in some embodiments 75%-85%. The measuring of a strut 22 length is discussed above in regard to FIG. 3. With peak 26 to peak 26 connector struts 20, as shown in FIGS. 10A and 9A, mirror images of this node 39 construction and positioning are presented in adjacent expansion columns 119.

FIG. 10A shows the as-cut configuration of an embodiment of the invention. In some embodiments, angle 168 may be up to four times the size of angle 32. In some embodiments, angle 168 may be up to six times the size of angle 32. Angle 166 is a function of angles 168 and 32. It 166 is about equal to half the size of angle 168 plus one half the size of angle 32. The size of angle 166 may be up to 4.5 times the size of angle 32.

FIG. 10B illustrates the portion of a stent shown in FIG. 10A crimped down into a contracted configuration. As can be seen, the differences between the non-node associated opening angles 32 and the angles 166, 168 associated with a peak connector node 39 are decreased to a point where they all are essentially closed. Due to crimping, the struts 22 may be curved and warped such that the angles produced are essentially zero.

FIG. 10C illustrates the portion of a stent shown in FIGS. 9A and 9B expanded to its deployed configuration. This expansion is achieved through self-expansion, such as with self-expanding stents, or through forced expansion, such as with a balloon. As can be seen, in this configuration, the differences between the non-node associated opening angles 32 and the opening angles 166 and 168 are substantially similar.

In addition and in combination to the embodiments of the invention described and claimed herein, the manipulation of stiffness of the strut pairs 41, 141, adjacent to an interconnecting strut 20 may also be achieved by increasing the stiffness of the strut pairs 41, 141, associated with a node 38, 39. This applies to strut pairs 41, 141, associated with peak 39 and/or valley 38 connector nodes. Increasing the stiffness of struts 41, 141, may be accomplished in a number of ways including, but not limited to increasing the width of the struts 41, 141.

Figure 11:
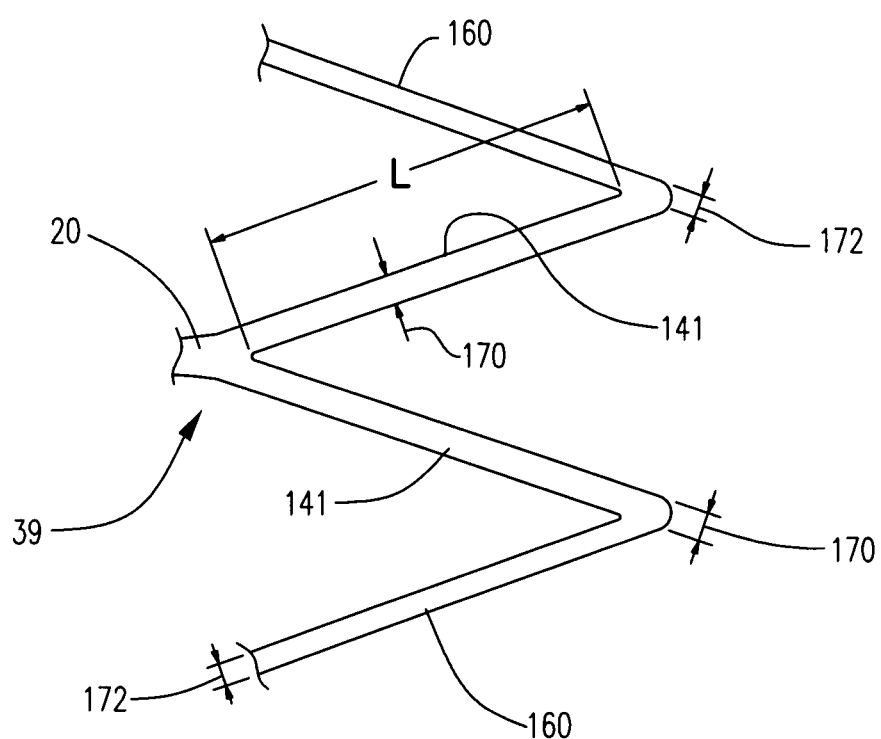
FIG. 11 is a partial side view of an embodiment of the invention.

FIG. 11 illustrates a portion of an embodiment of the present invention showing struts 141 associated with a peak connector node 39 and adjacent struts 160 not associated with the peak connector node 39. In this embodiment, struts pairs 141 are stiffened by increasing their width relative to strut pairs 160. As can be seen in FIG. 11, the width 170 of the struts of strut pair 141 is wider than the width 172 of the struts of strut pairs 160.

In some embodiments, width 170 may be about 15 to 120% greater in width than width 172. In some embodiments, width 170 may be about 20 to 90% greater in width than width 172. In some embodiments, width 170 may be about 40 to 70% greater in width than width 172. In some embodiments, the ratio comparisons are substantially along the entire effective strut lengths of the compared struts. In some embodiments, the ratio comparisons are substantially along at least 75% of the effective strut lengths of the compared struts. In some embodiments, the ratio comparisons are along the majority of the effective strut lengths of the compared struts.

In some embodiments, width 170 may be about 1.2 to 2.5 times the size of width 172. In some embodiments, width 170 may be about 1.4 to 2 times the size of width 172. In some embodiments, width 170 may be about 1.4 to 1.6 times the size of width 172. In some embodiments, the ratio comparisons are substantially along the entire effective strut lengths of the compared struts. In some embodiments, the ratio comparisons are substantially along at least 75% of the effective strut lengths of the compared struts. In some embodiments, the ratio comparisons are along the majority of the effective strut lengths of the compared struts.

In some embodiments, as mentioned herein, the struts 41, 141, associated with a peak connector node 39 or a valley connector node 38 are stiffer than adjacent struts 60, 160, that are not associated with the peak connector node 39. This may also apply to struts 22 that are not associated with a connector node 38, 39, and are not adjacent to strut pairs 41 and 141. The stiffness in the struts of strut pairs 41 and 141 may be increased in a number of ways including, but not limited to, the manners described herein. The degree of stiffness of the struts may be measured in suitable manners known in the field, including, but limited to Finite Element Analysis. The following equation may also be used to determine strut stiffness.

$$\text{Stiffness} = W^3 * T/L^2$$

W=strut width T=wall thickness L=effective strut length

In FIG. 11, the strut widths (W) is shown at 170 and 172 and the effective strut length (L) is indicated by "L". The wall thickness (T) is not shown, but is considered to be the measurement of the strut material down into the page.

In some embodiments, the stiffness of the strut pairs 41, 141, is greater than that of struts 22, 60, 160, not associated with a connector node. In some embodiments, the strut pairs 41 and 141 are at least 1.2 times as stiff. In some embodiments, the strut pairs 41 and 141 are at least 1.5 times as stiff. In some embodiments, the strut pairs 41 and 141 are at least 2 times as stiff. In some embodiments, the strut pairs 41 and 141 are at least 2.5 times as stiff.

The occurrence of valley connector nodes 38 and peak connector nodes 138 may vary in number and arrangement along the serpentine bands 19. Interconnecting struts also may vary in number and attachment points.

In the above-discussed embodiments, the inventive stents may be of substantially uniform diameter. It is also within the scope of the invention to modify the stent patterns discussed above to prepare stents of non-constant diameter. For example, stent which taper in the expanded state may be made by decreasing the amplitude of the serpentine bands from one end of the stent to the other, or just along a desired portion of the stent. A tapered portion may be provided anywhere along the stent. For example, half of the stent, starting at one end of the stent, may be provided with a taper. Another way to achieve a tapered expanded stent is to change the stiffness of the serpentine bands and/or the connectors such that the stiffness of the serpentine bands and/or connectors varies along the length of the stent. The stiffness of the serpentine bands and/or connectors can be changed by altering length, width or thickness or overall girth, adding additional stiffening material, using a chemical or mechanical means to alter the physical properties of the stent material, or applying one or a series of elastic elements about the stent.

The inventive stent patterns disclosed herein may also be used in conjunction with other known stent designs to provide stents whose properties vary over the length or portions thereof.

The invention is further directed to methods of manufacturing a stent according to the designs disclosed herein. The invention is further directed to methods of delivering and expanding a stent as described herein.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials that are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The present invention may be incorporated into both of the two basic types of catheters used in combination with a guide wire, commonly referred to as over-the-wire (OTW) catheters and rapid-exchange (RX) catheters. The construction and use of both over-the-wire and rapid-exchange catheters are well known in the art.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate The inventive stents may further comprise a polymer coating in addition to or in place of the therapeutic coating. Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions, for example, BAYHDROL®, fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. In a particular desirable embodiment of the invention, the polymer is a copolymer of polylactic acid and polycaprolactone.

In use, the stents disclosed herein are typically delivered via catheter to a desired bodily location. The choice of catheter will depend on the type of stent that is used and on the location to which the stent is delivered.

Any suitable method may be used to manufacture the inventive stents. For example, in addition to the methods listed above, the inventive stents may also be manufactured by preparing individual portions of the stent and connecting them to one another via welding, the use of adhesives or any other suitable joining technique. This list of manufacturing techniques is not meant to be exhaustive. Other manufacturing techniques may also be used to manufacture the inventive stents.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 4 may be taken as alternatively dependent on claim 2, or on claim 3; claim 5 may be taken as alternatively dependent from any of claims 1-3, etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent having a proximal end, a distal end, and a longitudinal axis extending through the proximal and distal ends, the stent further comprising:
    a plurality of interconnected serpentine bands, each serpentine band axially spaced from an immediately adjacent serpentine band, wherein each serpentine band comprises a plurality of struts, each strut of the serpentine band connected to a circumferentially adjacent strut in the serpentine band to form a juncture, wherein each juncture forms a peak and a valley, wherein the junctures include junctures which form peak connector nodes and junctures which form valley connector nodes,
    wherein each serpentine band is axially connected to the immediately adjacent serpentine band by at least one interconnecting member, each interconnecting member directly connects one peak connector node of one serpentine band to one valley connector node of the immediately adjacent serpentine band, wherein the valley connector node has a length in the axial direction between the peak and the valley, and the peak connector node has a length in the axial direction between the peak and the valley, wherein the length of the valley connector node is greater than the length of the peak connector node.

2. The stent of claim 1, wherein each valley connector node formed by a juncture has a circumferential width that is at least a combined strut width of the one interconnecting member and the two struts of the juncture, wherein the two struts comprise a first strut and a second strut.

3. The stent of claim 2, wherein for each valley connector node, a first node valley is formed between the first strut and the interconnecting member, a second node valley is formed between the second strut and the interconnecting member, the first and second node valleys each having a bottom center point, wherein the bottom center point of the first node valley is at a point that is between 3/16 and 1/2 of a length of the first strut and the bottom center point of the second node valley is at a point that is between 3/16 and 1/2 of a length of the second strut.

4. The stent of claim 3, wherein the bottom center point of the first node valley is at a point that is between 1/4 and 7/16 of the length of the first strut and the bottom center point of the second node valley is at a point that is between 1/4 and 7/16 of the length of the second strut.

5. The stent of claim 3, wherein the bottom center point of the first node valley is at a point that is between 1/4 and 3/8 of the length of the first strut and the bottom center point of the second node valley is at a point that is between 1/4 and 3/8 of the length of the second strut.

6. The stent of claim 3, wherein the bottom center point of the first node valley is at a point that is about 5/16 of the length of the first strut and the bottom center point of the second node valley is at a point that is about 5/16 of the length of the second strut.

7. The stent of claim 2, wherein each valley connector node has a peak of constant curvature.

8. The stent of claim 2, wherein, within at least one of the serpentine bands, each of the two struts associated with the valley connector node is shorter than a strut circumferentially adjacent to one of the two struts.

9. The stent of claim 8, wherein each of the two struts associated with the valley connector node is about 75%-90% of a length of the strut circumferentially adjacent to one of the two struts.

10. The stent of claim 8, wherein each of the two struts associated with the valley connector node is about 75%-85% of a length of the strut circumferentially adjacent to one of the two struts.

11. The stent of claim 2 wherein, within at least one of the serpentine bands, each of the two struts associated with the valley connector node have a greater girth than a strut circumferentially adjacent to one of the two struts.

12. The stent of claim 2, wherein, within at least one of the serpentine bands, each of the two struts associated with the valley connector node have a greater width than a strut circumferentially adjacent to one of the two struts.

13. The stent of claim 12, wherein each of the two struts associated with the valley connector node are about 1.2 to 2.5 times the width of the strut circumferentially adjacent to one of the two struts.

14. The stent of claim 12, wherein each of the two struts associated with the valley connector node are about 1.4 to 2 times the width of the strut circumferentially adjacent to one of the two struts.

15. The stent of claim 12, wherein each of the two struts associated with the valley connector node are about 1.4 to 1.6 times the width of the strut circumferentially adjacent to one of the two struts.

16. The stent of claim 2, wherein each of the two struts associated with the valley connector node have a greater width substantially along at least majority of their effective strut lengths than a strut circumferentially adjacent to one of the two struts.

17. The stent of claim 16, wherein each of the two struts associated with the valley connector node have a greater width substantially along at least 75% of their effective strut lengths than the strut circumferentially adjacent to one of the two struts.

18. The stent of claim 17, wherein each of the two struts associated with the valley connector node have a greater width substantially along at least 75% of their effective strut lengths than the strut circumferentially adjacent to one of the two struts.

19. The stent of claim 2, wherein, within at least one of the serpentine bands, a plurality of interconnecting struts that are associated with valley connector nodes are longer than a plurality of interconnecting struts that are not associated with valley connector nodes.

20. The stent of claim 2, wherein each of the two struts associated with the valley connector node are at least 1.2 times as stiff as a strut circumferentially adjacent to one of the two struts.

21. The stent of claim 2, wherein each of the two struts associated with the valley connector node are at least 1.5 times as stiff as the strut circumferentially adjacent to one of the two struts.

22. The stent of claim 2, wherein each of the two struts associated with the valley connector node are at least 2 times as stiff as the strut circumferentially adjacent to one of the two struts.

23. The stent of claim 2, wherein each of the two struts associated with the valley connector node are at least 2.5 times as stiff as the strut circumferentially adjacent to one of the two struts.

24. The stent of claim 1, wherein the stent has an as-cut state,
wherein the interconnecting member and a first strut associated with the valley connector node form a first opening angle; wherein the first strut and a second strut circumferentially adjacent to the first strut form a second opening angle, wherein the second strut and a third strut circumferentially adjacent to the second strut form a third opening angle;
wherein, when the stent is in its as-cut state, the first opening angle has a greater magnitude than a magnitude of the third opening angle.

25. The stent of claim 24, wherein, when the stent is in its as-cut state, a magnitude of the second opening angle is greater than the magnitude of the third opening angle.

26. The stent of claim 1, wherein the struts associated with the valley connector nodes are stiffer than the struts that are not associated with the valley connector nodes, where stiffness is measured using finite element analysis or the equation $$\text{Stiffness} = W^3 * T/L^2,$$

wherein W=strut width, T=wall thickness and L=effective strut length.

27. The stent of claim 1, wherein the two struts associated with each valley connector node form an opening angle that is open in a first direction, and all of the opening angles in all of the serpentine bands are open in the same direction.

28. The stent of claim 27, wherein the two struts associated with each peak connector node form an opening angle that is open in a second direction, wherein the second direction is the same as the first direction.

29. A stent delivery system comprising a catheter having a distal portion and a stent according to claim 1.

30. A method of delivering a stent to a site comprising the steps of providing a stent delivery system, the stent delivery system comprising:
a stent delivery catheter, and
a stent according to claim 1,
advancing the stent delivery system to a vessels site; and
deploying the stent at the vessel site.

* * * * *